US010828169B2

(12) United States Patent
Britton et al.

(10) Patent No.: US 10,828,169 B2
(45) Date of Patent: Nov. 10, 2020

(54) STEMLESS SHOULDER IMPLANT

(71) Applicant: Zimmer, Inc., Warsaw, IN (US)

(72) Inventors: Orsa Britton, Warsaw, IN (US); David A. Nolan, Fort Wayne, IN (US); Andrew Hopkins, Winterthur (CH); Stephen J Vankoski, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/293,373

(22) Filed: Oct. 14, 2016

(65) Prior Publication Data
US 2017/0105843 A1  Apr. 20, 2017

Related U.S. Application Data

(60) Provisional application No. 62/241,858, filed on Oct. 15, 2015.

(51) Int. Cl.
*A61F 2/40* (2006.01)
*A61F 2/30* (2006.01)

(52) U.S. Cl.
CPC .............. *A61F 2/4081* (2013.01); *A61F 2/40* (2013.01); *A61F 2/4003* (2013.01); *A61F 2/4014* (2013.01); *A61F 2002/30642* (2013.01); *A61F 2002/4022* (2013.01); *A61F 2002/4085* (2013.01); *A61F 2002/4088* (2013.01);
(Continued)

(58) Field of Classification Search
CPC ............................................. A61F 2/40–4081
See application file for complete search history.

(56) References Cited

U.S. PATENT DOCUMENTS

| 4,003,095 A | 1/1977 | Gristina |
| 5,336,267 A | 8/1994 | Kubein-meesenburg et al. |

(Continued)

FOREIGN PATENT DOCUMENTS

| CN | 108697509 A | 10/2018 |
| EP | 0850609 A1 | 7/1998 |

(Continued)

OTHER PUBLICATIONS

"U.S. Appl. No. 14/439,605, Notice of Allowance dated Feb. 2, 2017", 5 pgs.
(Continued)

*Primary Examiner* — Marcia L Watkins
(74) *Attorney, Agent, or Firm* — Schwegman Lundberg & Woessner, P.A.

(57) ABSTRACT

The present disclosure provides a shoulder prosthesis. The shoulder prosthesis includes a glenoid component, a humeral component, and an articulation component. The glenoid component includes a glenoid body having a proximal side and a distal side, the proximal side shaped to engage with a resected portion of a glenoid cavity. The humeral component includes a humeral body having a proximal side and a distal side, the distal side shaped to engage with a resected portion of a humerus. The articulation component is positionable between the distal side of the glenoid component and the proximal side of the humeral component, the articulation component configured to be maintained between the glenoid and humeral components, after implantation, by at least one of a deltoid muscle and a rotator cuff.

17 Claims, 11 Drawing Sheets

(52) U.S. Cl.
CPC ............... *A61F 2310/00029* (2013.01); *A61F 2310/00131* (2013.01); *A61F 2310/00179* (2013.01)

(56) References Cited

U.S. PATENT DOCUMENTS

| | | | |
|---|---|---|---|
| 5,593,445 | A | 1/1997 | Waits |
| 5,723,018 | A | 3/1998 | Cyprien et al. |
| 7,033,396 | B2 | 4/2006 | Tornier |
| 7,241,314 | B1 | 7/2007 | Winslow |
| 7,799,077 | B2 | 9/2010 | Lang et al. |
| 8,425,614 | B2 * | 4/2013 | Winslow ............... A61F 2/4003 623/19.11 |
| 9,408,652 | B2 | 8/2016 | Hassler et al. |
| 9,763,797 | B2 | 9/2017 | Hopkins et al. |
| 10,687,949 | B2 | 6/2020 | Hopkins et al. |
| 2004/0220673 | A1 * | 11/2004 | Pria ...................... A61F 2/4081 623/19.12 |
| 2006/0009852 | A1 | 1/2006 | Winslow et al. |
| 2009/0112328 | A1 | 4/2009 | Tornier et al. |
| 2009/0287309 | A1 | 11/2009 | Walch et al. |
| 2011/0098822 | A1 | 4/2011 | Walch et al. |
| 2011/0118846 | A1 * | 5/2011 | Katrana ................ A61F 2/4014 623/19.13 |
| 2011/0264153 | A1 * | 10/2011 | Hassler .............. A61B 17/1684 606/86 R |
| 2013/0053969 | A1 | 2/2013 | Linares et al. |
| 2015/0289985 | A1 | 10/2015 | Hopkins |
| 2017/0348111 | A1 | 12/2017 | Hopkins et al. |

FOREIGN PATENT DOCUMENTS

| | | |
|---|---|---|
| EP | 1393697 B1 | 2/2006 |
| EP | 1649836 A2 | 4/2006 |
| EP | 1598034 B1 | 3/2011 |
| EP | 2382930 A1 | 11/2011 |
| EP | 2749255 A1 | 7/2014 |
| JP | H06189987 A | 7/1994 |
| JP | 2007202965 A | 8/2007 |
| JP | 2018530397 A | 10/2018 |
| WO | WO-9410941 | 5/1994 |
| WO | WO-2007057054 A1 | 5/2007 |
| WO | WO-2012125704 A2 | 9/2012 |
| WO | WO-2014102141 A1 | 7/2014 |
| WO | WO-2017066504 A1 | 4/2017 |

OTHER PUBLICATIONS

"U.S. Appl. No. 14/439,605, Response filed Jan. 12, 2017 to Final Office Action dated Oct. 12, 2016", 16 pgs.
"International Application Serial No. PCT/US2016/056935, International Search Report dated Jan. 18, 2017", 6 pgs.
"International Application Serial No. PCT/US2016/056935, Written Opinion dated Jan. 18, 2017", 7 pgs.
"U.S. Appl. No. 14/439,605, Final Office Action dated Oct. 12, 2016", 12 pgs.
"U.S. Appl. No. 14/439,605, Non Final Office Action dated Mar. 16, 2016", 11 pgs.
"U.S. Appl. No. 14/439,605, Preliminary Amendment filed Apr. 29, 2015", 9 pgs.
"U.S. Appl. No. 14/439,605, Response filed Aug. 5, 2016 to Non Final Office Action dated Mar. 16, 2016", 13 pgs.
"International Application Serial No. PCT/EP2013/077419, International Preliminary Report on Patentability dated Jun. 30, 2015", 9 pgs.
"International Application Serial No. PCT/EP2013/077419, International Search Report dated Jan. 30, 2014", 5 pgs.
"U.S. Appl. No. 14/439,605, Notice of Allowance dated May 25, 2017", 5 pgs.
"U.S. Appl. No. 15/684,578, Preliminary Amendment filed Sep. 29, 2017", 6 pgs.
"International Application Serial No. PCT/US2016/056935, International Preliminary Report on Patentability dated Apr. 26, 2018", 9 pgs.
"Australian Application Serial No. 2016339995, First Examination Report dated Jul. 20, 2018", 3 pgs.
"Australian Application Serial No. 2016339995, Subsequent Examiners Report dated Sep. 12, 2018", 4 pgs.
"U.S. Appl. No. 15/684,578, Final Office Action dated Jun. 13, 2019", 6 pgs.
"U.S. Appl. No. 15/684,578, Non Final Office Action dated Mar. 21, 2019", 12 pgs.
"U.S. Appl. No. 15/684,578, Response filed Feb. 27, 2019 to Restriction Requirement dated Jan. 10, 2019", 8 pgs.
"U.S. Appl. No. 15/684,578, Response Filed Apr. 26, 2019 to Non-Final Office Action dated Mar. 21, 2019", 13 pgs.
"U.S. Appl. No. 15/684,578, Restriction Requirement dated Jan. 10, 2019", 6 pgs.
"Canadian Application Serial No. 3,001,838, Examiner's Rule 30(2) Requisition dated Aug. 8, 2019", 5 pgs.
"European Application Serial No. 16787980.8, Response filed Jan. 7, 2019 to Office Action dated Jul. 26, 2018", 13 pgs.
"Japanese Application Serial No. 2018-519286, Notification of Reasons for Rejection dated Mar. 26, 2019", w/ English Translation, 11 pgs.
"Japanese Application Serial No. 2018-519286, Response filed Jun. 19, 2019 to Notification of Reasons for Rejection dated Mar. 26, 2019", w/o English claims, 6 pgs.
"U.S. Appl. No. 15/684,578, Non Final Office Action dated Oct. 7, 2019", 7 pgs.
"U.S. Appl. No. 15/684,578, Notice of Allowance dated Jan. 29, 2020", 9 pgs.
"U.S. Appl. No. 15/684,578, Response filed Jan. 7, 2020 to Non Final Office Action dated Oct. 7, 2019", 11 pgs.
"U.S. Appl. No. 15/684,578, Response Filed Sep. 13, 2019 to Final Office Action dated Jun. 13, 2019", 11 pgs.
"U.S. Appl. No. 15/684,578, Supplemental Notice of Allowability dated Apr. 3, 2020", 3 pgs.
"Canadian Application Serial No. 3,001,838, Response filed Feb. 4, 2020 to Examiner's Rule 30(2) Requisition dated Aug. 8, 2019", 3 pgs.
"Chinese Application Serial No. 201680069210.3, Office Action dated Mar. 30, 2020", (W/ English Translation), 5 pgs.
"Chinese Application Serial No. 201680069210.3, Office Action dated Aug. 14, 2019", (W/ English Translation), 6 pgs.
"Chinese Application Serial No. 201680069210.3, Response filed Nov. 15, 2019 to Office Action dated Aug. 14, 2019", (W/ English Translation of Claims), 9 pgs.
"Canadian Application Serial No. 3,001,838, Office Action dated Apr. 21, 2020", 5 pages.
"U.S. Appl. No. 15/684,578, Supplemental Notice of Allowability dated May 28, 2020", 3 pages.
"Canadian Application Serial No. 3,001,838, Response filed Aug. 20, 2020 to Office Action dated Apr. 21, 2020", 9 pgs.
"Chinese Application Serial No. 201680069210.3, Office Action dated Aug. 27, 2020", (W/ English Translation), 14 pgs.
"Chinese Application Serial No. 201680069210.3, Response filed Sep. 27, 2020 to Office Action dated Aug. 27, 2020", (W/ English Translation), 11 pgs.

* cited by examiner

STEMLESS SHOULDER IMPLANT

CROSS-REFERENCE TO RELATED APPLICATIONS

The present application claims the benefit of priority to U.S. Provisional Application No. 62/241,858, filed Oct. 15, 2015, the contents of which is hereby incorporated by reference in its entirety.

The present application is related to U.S. Non-Provisional application Ser. No. 14/439,605, filed Dec. 19, 2013, which is a National Stage Application of PCT/EP2013/077419, the contents of which are hereby incorporated by reference in their entirety.

FIELD OF THE DISCLOSURE

The present disclosure relates to surgical implant systems, including implants, and methods for performing a total shoulder arthroplasty, a hemi shoulder arthroplasty, or a reverse total shoulder arthroplasty.

BACKGROUND

In a healthy shoulder, the proximal humerus is generally ball-shaped, and articulates within a socket, called the glenoid, formed by the scapula to form the shoulder joint. Conventional implant systems for the total replacement of the shoulder joint due to disease or trauma, i.e., a total shoulder arthroplasty, generally replicate the natural anatomy of the shoulder, and typically include a humeral component having a stem which fits within the humeral canal, and an articulating head which articulates within the socket of a glenoid component implanted within the glenoid of the scapula. An implant system for the replacement of only the humeral component of the shoulder joint, i.e., a hemi shoulder arthroplasty, typically includes only a humeral component which articulates within the natural glenoid socket of the scapula.

In addition, "reverse" type implant systems have been developed in which the conventional ball-and-socket configuration that replicates the natural anatomy of the shoulder is reversed, such that a concave recessed articulating component is provided at the proximal end of the humeral component that articulates against a convex portion of the glenoid component. Such reverse shoulder implant systems are thought to provide an increased range of motion for treatment of glenohumeral arthritis associated with irreparable rotator cuff damage, for example, by moving the center of rotation between the humeral component and the glenoid component to allow the deltoid muscles to exert a greater lever arm on the humerus.

SUMMARY

To better illustrate the system disclosed herein, a non-limiting list of examples is provided here:

In Example 1, a shoulder prosthesis can be provided that includes a glenoid component, a humeral component, and an articulation component. The glenoid component includes a glenoid body having a proximal, or medial, side and a distal, or lateral, side, the proximal side shaped to engage with a resected portion of a glenoid cavity. The humeral component includes a humeral body having a proximal side and a distal side, the distal side shaped to engage with a resected portion of a humerus. The articulation component is positionable between the distal side of the glenoid component and the proximal side of the humeral component, the articulation component configured to be maintained between the glenoid and humeral components, after implantation, by at least a deltoid muscle and a rotator cuff muscle.

In Example 2, the shoulder prosthesis of Example 1 is optionally configured such that the glenoid component further includes a glenoid articular layer on the distal side of the glenoid body, and where the humeral component further includes a humeral articular layer on the proximal side of the humeral body.

In Example 3, the shoulder prosthesis of any one of or any combination of Examples 1-2 is optionally configured such that the glenoid body and the humeral body are at least partially formed from a porous metal.

In Example 4, the shoulder prosthesis of Example 3 is optionally configured such that the porous metal comprises tantalum.

In Example 5, the shoulder prosthesis of any of Examples 2-4 is optionally configured such that at least one of the glenoid articular layer and the humeral articular layer comprises a ceramic material.

In Example 6, the shoulder prosthesis of any of Examples 2-4 is optionally configured such that at least one of the glenoid articular layer and the humeral articular layer comprises a vitamin E stabilized polyethylene or a cobalt chrome.

In Example 7, the shoulder prosthesis of any of Examples 1-6 is optionally configured such that the glenoid component and the humeral component are attachable to the resected portion of the glenoid cavity and the resected portion of the humerus, respectively, using bone cement.

In Example 8, the shoulder prosthesis of any of Examples 1-7 is optionally configured such that the glenoid component and the humeral component are attachable to the resected portion of the glenoid cavity and the resected portion of the humerus, respectively, using one or more fasteners.

In Example 9, the shoulder prosthesis of any of Examples 1-8 is optionally configured such that at least one of the glenoid component and the humeral component includes a peg configured to be received within a bone recess.

In Example 10, the shoulder prosthesis of Example 9 is optionally configured such that the peg comprises a fluted peg.

In Example 11, the shoulder prosthesis of any of Examples 2-10 is optionally configured such that the glenoid articular layer and the humeral articular layer each include a concave articular surface.

In Example 12, the shoulder prosthesis of Example 11 is optionally configured such that the articulation component includes an outer surface having at least a first convex portion configured to mate with the concave articular surface of the glenoid articular layer and a second convex portion configured to mate with the concave articular surface of the humeral articular layer.

In Example 13, the shoulder prosthesis of Example 12 is optionally configured such that the articulation component is generally spherical.

In Example 14, the shoulder prosthesis of Example 12 is optionally configured such that the articulation component has an ovoid shape.

In Example 15, the shoulder prosthesis of any of Examples 2-10 is optionally configured such that the glenoid articular layer and the humeral articular layer each include a convex articular surface.

In Example 16, the shoulder prosthesis of Example 15 is optionally configured such that the articulation component includes an outer surface having at least a first concave portion configured to mate with the convex articular surface of the glenoid articular layer and a second concave portion configured to mate with the convex articular surface of the humeral articular layer.

In Example 17, the shoulder prosthesis of any of Examples 1-16 is optionally configured such that the articulation component is at least partially formed from a ceramic, a vitamin E stabilized polyethylene, a pyrolytic carbon, or a cobalt chrome.

In Example 18, a shoulder prosthesis can be provided that includes a glenoid component, a humeral component, and an articulation component. The glenoid component can include a glenoid body and a glenoid articular surface. The glenoid body can be shaped to engage with a resected portion of a glenoid cavity. The humeral component can include a humeral body and a humeral articular surface. The humeral body can be shaped to engage with a resected portion of a humerus. The articulation component can be positionable between the glenoid articular surface and the humeral articular surface. The articulation component can be configured to be held in place, after implantation, by at least a deltoid muscle and a rotator cuff muscle.

In Example 19, the shoulder prosthesis of Example 18 is optionally configured such that the glenoid body and the humeral body are formed from a first material, and the glenoid articular surface and the humeral articular surface are formed from a second material different than the first material.

In Example 20, a method for installing a shoulder prosthesis can be provided. The method can include forming an incision in an axilla region of a patient; resecting, through the incision, a portion of a humerus; resecting, through the incision, a portion of a glenoid cavity; inserting a humeral component through the incision; attaching the bone contacting surface of the humeral component to the resected portion of the humerus; inserting a glenoid component through the incision; attaching the bone contacting surface of the glenoid component to the resected portion of the glenoid cavity; and inserting an articulation component through the incision and between the articular surfaces of the humeral and glenoid components. The humeral component includes a bone contacting surface and an opposing articular surface. The bone contacting surface of the humeral component is shaped to mate with the resected portion of the humerus. The glenoid component includes a bone contacting surface and an opposing articular surface. The bone contacting surface of the glenoid component is shaped to mate with the resected portion of the glenoid cavity. The articulation component is held between the humeral and glenoid components by at least a deltoid muscle and a rotator cuff muscle.

In Example 21, attaching the bone contacting surface of the humeral component to the resected portion of the humerus of the method in Example 20 optionally includes applying bone cement to at least one of the bone contacting surface and the resected portion of the humerus.

In Example 22, attaching the bone contacting surface of the glenoid component to the resected portion of the glenoid cavity of the method in Examples 20 or 21 optionally includes applying bone cement to at least one of the bone contacting surface and the resected portion of the glenoid cavity.

In Example 23, attaching the bone contacting surface of the humeral component to the resected portion of the humerus of the method in any of Example 20-22 optionally includes inserting a bone fastener through the humeral component and into the humerus.

In Example 24, attaching the bone contacting surface of the glenoid component to the resected portion of the glenoid cavity of the method in Examples 20-23 optionally includes inserting a bone fastener though the glenoid component and into the glenoid cavity.

In Example 25, the bone contacting surfaces of the humeral and glenoid components of Examples 20-24 optionally are at least partially formed from a porous metal that facilitates bone ingrowth after implantation of the humeral and glenoid components.

In Example 26, the shoulder prosthesis or method of any one of or any combination of Examples 1-25 is optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate example embodiments, and such examples are not to be construed as limiting the scope of the disclosure in any manner.

DETAILED DESCRIPTION

As used herein, the following directional definitions apply. Anterior and posterior mean nearer the front or nearer the rear of the body, respectively; proximal and distal mean nearer to or further front the root of a structure, respectively, and medial and lateral mean nearer the sagittal plane or further from the sagittal plane, respectively. The sagittal plane is an imaginary vertical plane through the middle of the body that divides the body into right and left halves.

Figure 1:
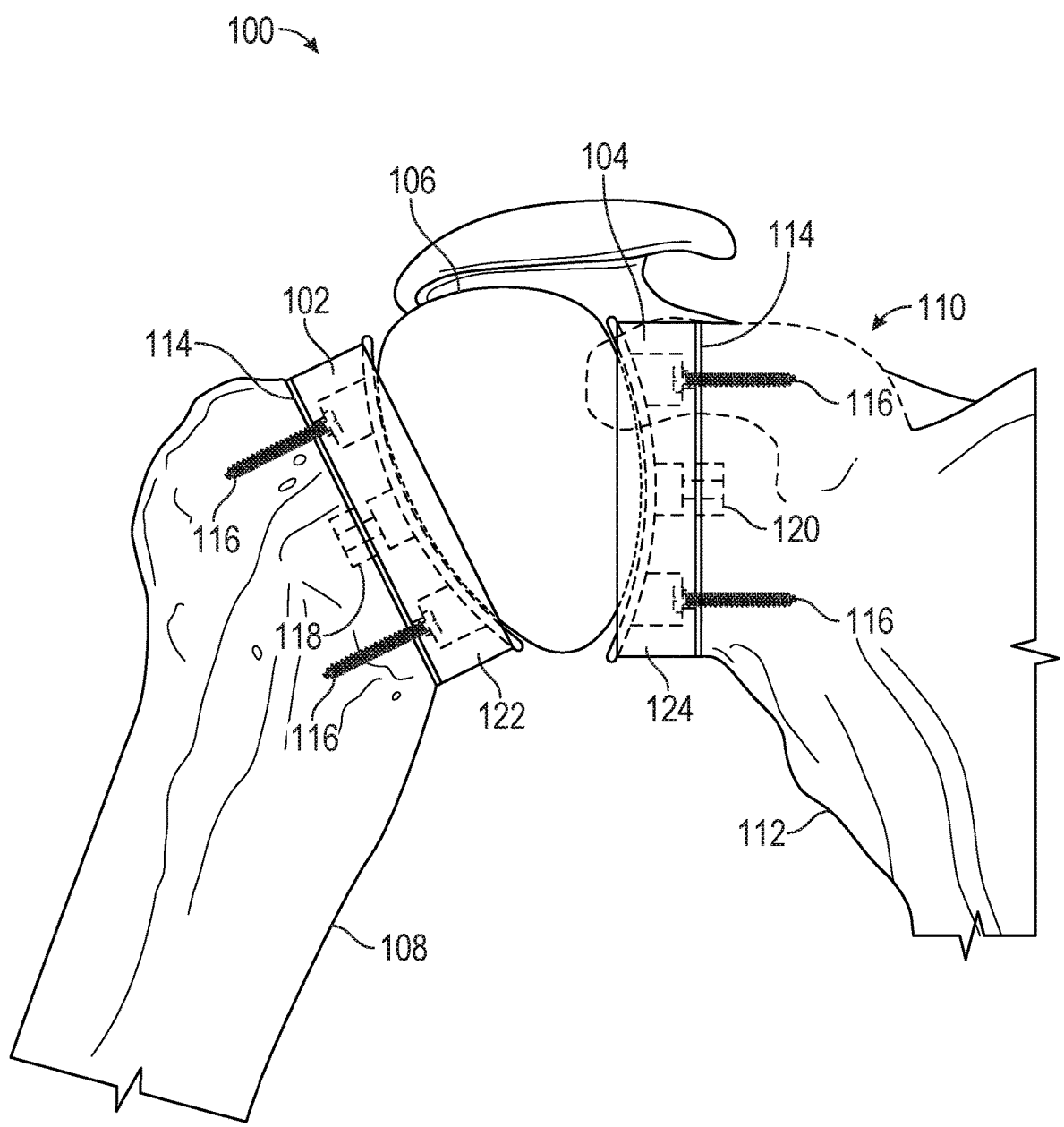
FIG. 1 shows an example of a stemless shoulder implant implanted within a shoulder.

Referring now to the figures, FIG. 1 shows a stemless shoulder implant 100 in accordance with at least one example of the present application. Stemless shoulder implant 100 can include a humeral component 102, a glenoid component 104, and an articulation component 106. Humeral component 102 can be attached to a humerus 108 and glenoid component 104 can be attached to a glenoid cavity 110 of a scapula 112. The interface between humerus 108 and humeral component 102 and the interface between glenoid cavity 110 and glenoid component 104 can be resected bone.

Figure 2A:
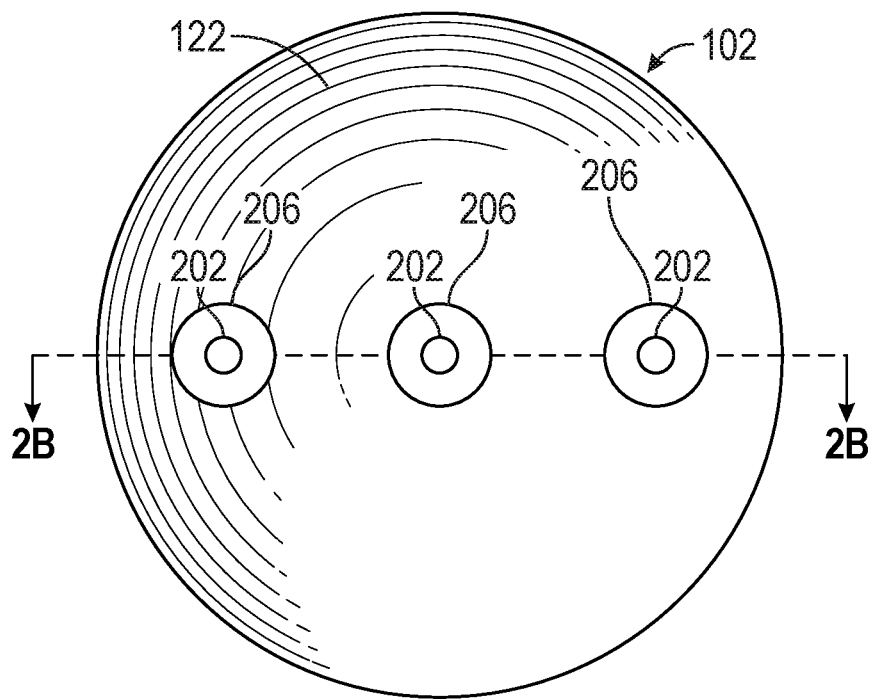
FIG. 2A shows a front view of an example humeral component having a concave articular surface.
Figure 2B:
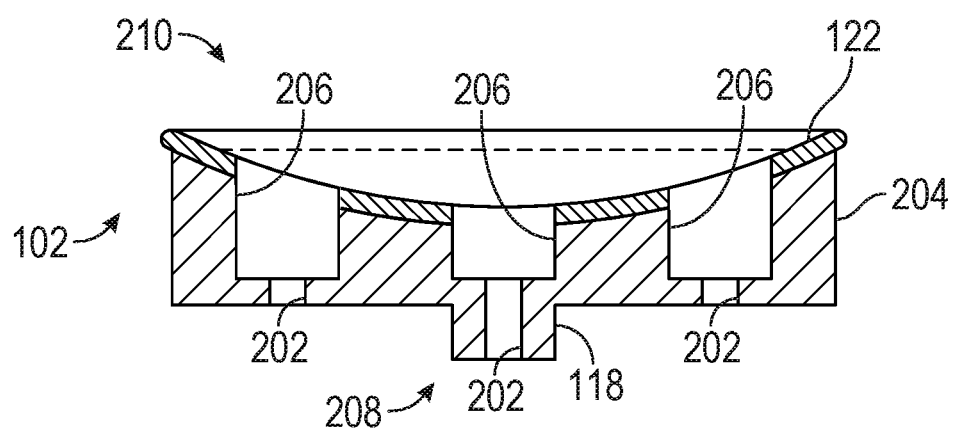
FIG. 2B shows a cross-sectional view of an example humeral component having a concave articular surface.
Figure 2C:
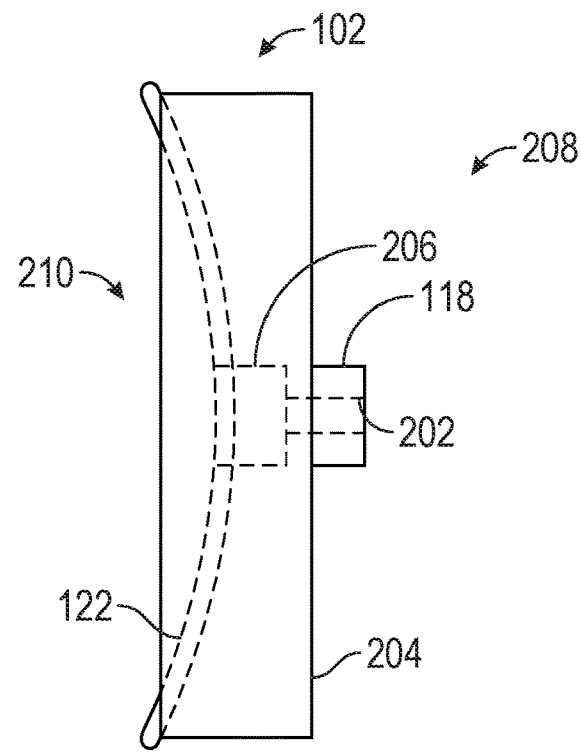
FIG. 2C shows a side view of an example humeral component having a concave articular surface.

Bone cement 114, bone screws 116, and/or other fasteners can be used to attach humeral component 102 to humerus 108 and glenoid component 104 to glenoid cavity 110. For example, and as shown in FIGS. 2A-2C, humeral component 102 and glenoid component 104 can each include one or more through holes 202. The through holes 202 can allow for bone screws 116 to pass through humeral component 102 and glenoid component 104 and into humerus 108 and glenoid cavity 110, respectively. Furthermore, bone cement 114 can be placed at various locations or coat the distal side of humeral component 102 and the proximal side of glenoid component 104. Bone cement 114 can be used with or without bone screws 116 to attach humeral component 102 to humerus 108 and glenoid component 104 to glenoid cavity 110.

Humeral component 102 can include a humeral peg 118 that extends from a distal side of the component and glenoid component 104 can include a glenoid peg 120 that extends from a proximal side of the component. Humeral peg 118 and glenoid peg 120 can be received within a recess located within humerus 108 and glenoid cavity 110, respectively. The proximal side of humeral component 102 can include a humeral articulation layer 122 and the distal side of glenoid component 104 can include a glenoid articulation layer 124.

Articulation component 106 can be "free floating" and disposed between, but not attached to, humeral articulation layer 122 and glenoid articulation layer 124. As discussed herein, humeral component 102 and glenoid component 104 each can include a concave portion. Articulation component 106 can be ovoid or circular in shape and can rest between the concave portions of humeral component 102 and glenoid component 104. As will be discussed below, during implantation articulation component 106 can be inserted via an incision in an axilla region of a patient or deltopectoris or deltoid splitting. After implantation, articulation component 106 can be held in place by a joint capsule of the shoulder.

The various components can be modular and part of a kit of components. For example, as discussed herein, humeral articulation layer 122 can be a separate component from humeral component 102 and glenoid articulation layer 124 can be separate component from glenoid component 104. Glenoid peg 120 and humeral peg 118 can also be separate components. As such, a surgeon can select the appropriate components during a surgery. For instance, during surgery a surgeon may decide to use a concave glenoid component 104 without glenoid articulation layer 124 and a convex humeral component (such as a humeral component 402 described below) with a humeral articulation layer (such as a humeral articulation layer 422 described below).

FIGS. 2A-2C show a glenoid component or a humeral component having concave articular surfaces, in accordance with at least one example of the present application. For simplicity, FIGS. 2A-2C will be referenced with respect to humeral component 102. However, the discussion of FIGS. 2A-2C also applies to glenoid component 104 as well.

Humeral component 102 can include a component body 204 that can include holes 202. Each of holes 202 can also include a recess 206. The recess 206 can allow a fastener, such as a bone screw 116, to be recessed into humeral component 102. Recess 206 can be filled with a plug or other filler (not shown) after humeral component 102 has been attached to humerus 108. Humeral component 102 can also include humeral peg 118, which can have a hole 202. Humeral peg 118 can also be fluted. Humeral component 102 can be formed of one or more materials. For example, humeral component 102 can be formed of a ceramic. In addition, humeral component 102 can be formed partially of a porous metal, such as tantalum, and partially of a non-porous metal such as stainless steel or cobalt chrome.

Humeral component 102 can be formed of a highly porous, three-dimensional metallic structure. A highly porous, three-dimensional metallic structure can incorporate one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing bony tissue or other tissue to grow into the porous structure over time to enhance fixation (e.g., osseointegration) between the structure and surrounding bodily structures. According to certain embodiments of the present disclosure, an open porous metal structure, or a portion thereof, may have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After, the fusing of the powder in each layer, an additional layer of powder is deposited, and a further fusing step is carried out, with fused portions or lateral layers fusing so as to fuse portions of previous laid layers until a three-dimensional article is complete. In cumin embodiments, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some embodiments, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

A highly porous, three-dimensional metallic structure may be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain embodiments, an open porous metal structure may be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure may have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

A distal side 208 can include humeral peg 118. In addition, distal side 208 can be shaped to engage a resected portion of humerus 108. Distal side 208 can be flat, concave, or convex. In addition, distal side 208 can have a custom profile. For example, using imaging techniques such as CT or MRI, humeral component 102 can be custom designed for a specific patient. As such, a physician can request that distal side 208 have a mixture of flat, concave, and convex portions to assist with mating humeral component 102 to humerus 108.

Humeral component 102 can also include a proximal side 210. Proximal side 210 can be concave in shape. The profile of proximal side 210 can correspond to a profile of articulation component 106. Having corresponding mating surfaces can allow humeral component 102 to move freely along articulation component 106.

Humeral articulation layer 122 can be attached to humeral component 102. Humeral articulation layer 122 can be formed on humeral component 102 via chemical vapor deposition. Humeral articulation layer 122 can be formed of a ceramic material. Humeral articulation layer 122 can also be formed of a polymer such as, but not limited to, a vitamin E stabilized polyethylene, sometimes referred to as a Vitamin E poly. A portion of humeral component 102 can also form humeral articulation layer 122. For example, a portion of humeral component 102 can be a polished metal that mates with a convex portion of articulation component 106.

Figure 3:
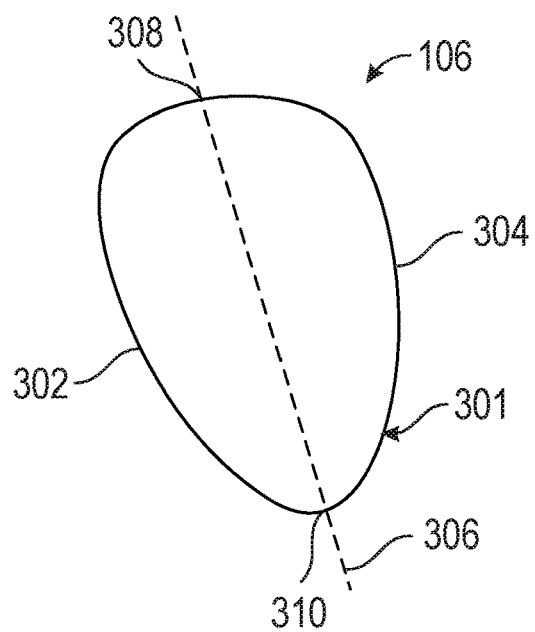
FIG. 3 shows an example articulation component having convex portions.

FIG. 3 shows an articulation component 106 in accordance with at least one example of the present application. Articulation component 106 can be generally spherical in shape. In addition, articulation component 106 can be generally ovoid or circular in shape.

Articulation component 106 can include an outer surface 301 that includes a first portion 302 that can be convex in shape. First portion 302 can be configured to mate with concave portion of proximal side 210 of humeral component 102. The outer surface of articulation component 106 can also include a second portion 304 that can be convex in shape. Second portion 304 can be configured to mate with a concave portion of glenoid component 104. A centerline 306 can extend from a first portion 308 of a perimeter defined by a cross-section of surface 301 to a second portion of the perimeter defined by the cross-section of surface 301. As shown in FIG. 3, articulation component 106 can be completely asymmetrical about centerline 306 and an other axis that can pass through articulation component 106. In an example, first portion 302 can be convex and second portion 304 can be concave to mate with corresponding concave and convex portions on humeral component 102 and glenoid component 104, respectively. In another example, first portion 302 can be concave and second portion 304 can be convex to mate with corresponding convex and concave portions on humeral component 102 and glenoid component 104, respectively.

Articulation component 106 can be formed of a polymer such as a vitamin E stabilized polyethylene. Articulation component 106 can be formed of a ceramic or metal, such as cobalt chrome. In an example, articulation component 106 can be formed of combinations of a polymer, ceramic, or metal. In an example, articulation component 106 can be formed from a balloon.

Articulation component 106 also can be formed using an inflatable membrane. For example, articulation component 106 can be formed of a pliable material such as, but not limited to, a vitamin E stabilized polyethylene or a biocompatible polymer. The pliable material can define a cavity into which a fluid or other flowable substance can be injected. Upon injection of the fluid, the cavity defined by the flowable material can inflate to fill avoid defined by the glenoid component 104 and the humeral component 102.

As disclosed herein, the glenoid component 104 and the humeral component 102 can define a void to receive the articulation component 106. Filling of the articulation component 106 after it is received within the void defined by the glenoid component 104 and the humeral component 102 can allow the articulation component to be custom sized by a surgeon during a surgical procedure. In addition, by inflating the pliable material within the void, trauma to the shoulder muscles, tendons, and ligaments can be minimized. For instance, because the articulation component 106 can have a reduced size when inserted into the void defined by the glenoid component 104 and the humeral component 102, stretching or otherwise disturbing muscles, tendons, and ligaments proximate the surgical site can be minimized as compared to inserting a fully formed articulation component 106. Furthermore, during a revision, the pliable material can be removed without damage to the glenoid component 104, the humeral component 102, or surrounding tissue.

Figure 4:
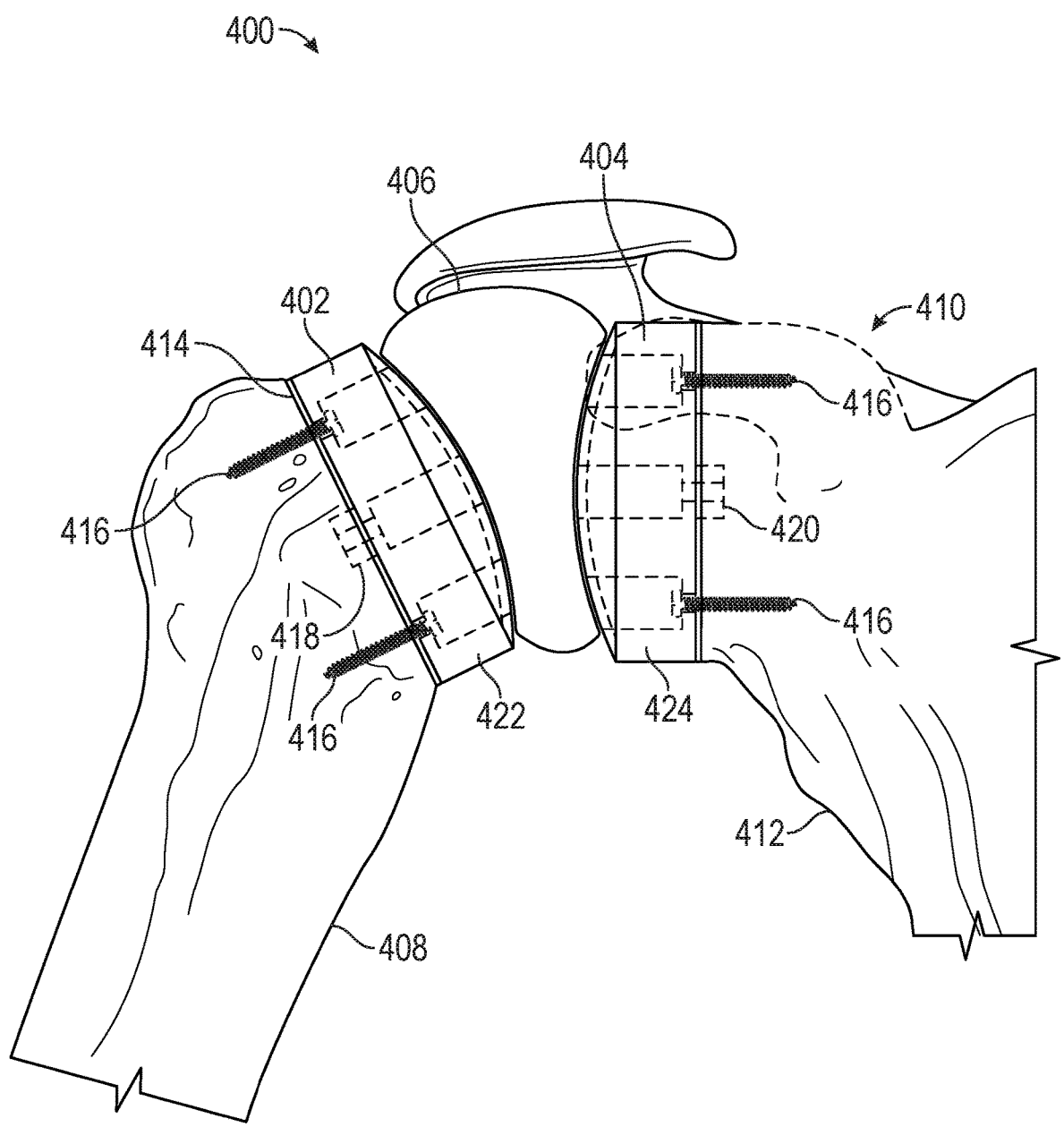
FIG. 4 shows an example of a stemless shoulder implant implanted within a shoulder.

FIG. 4 shows another stemless shoulder implant 400 in accordance with at least one example of the present application. Stemless shoulder implant 400 can include a humeral component 402, a glenoid component 404, and an articulation component 406. Humeral component 402 can be attached to a humerus 408 and glenoid component 404 can be attached to a glenoid cavity 410 of a scapula 412. The interface between humerus 408 and humeral component 402 and the interface between glenoid cavity 410 and glenoid component 404 can be resected bone.

Figure 5A:
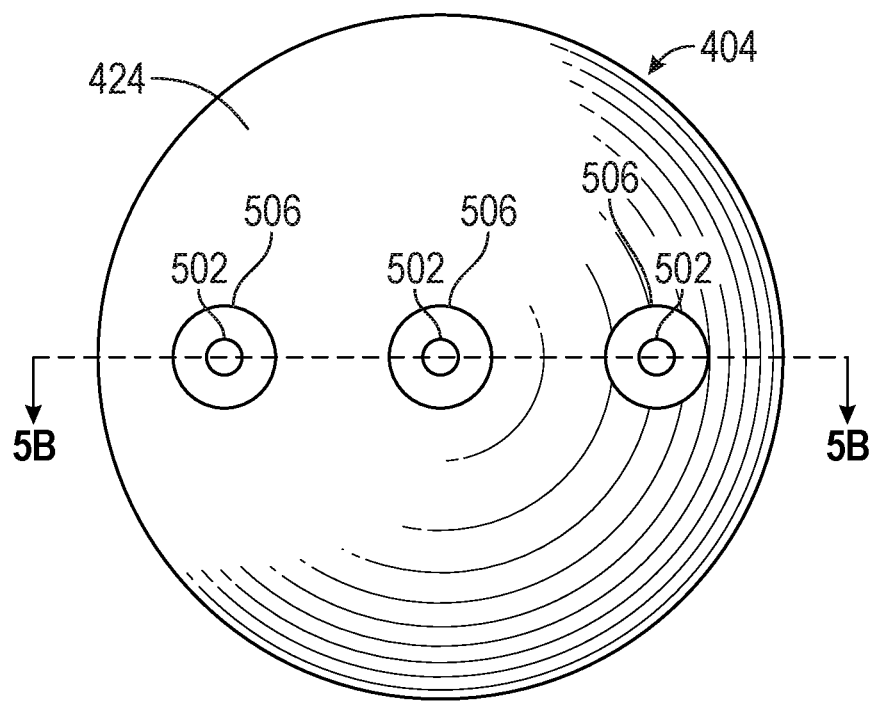
FIG. 5A shows a front view of an example glenoid component having a convex articular surface.
Figure 5B:
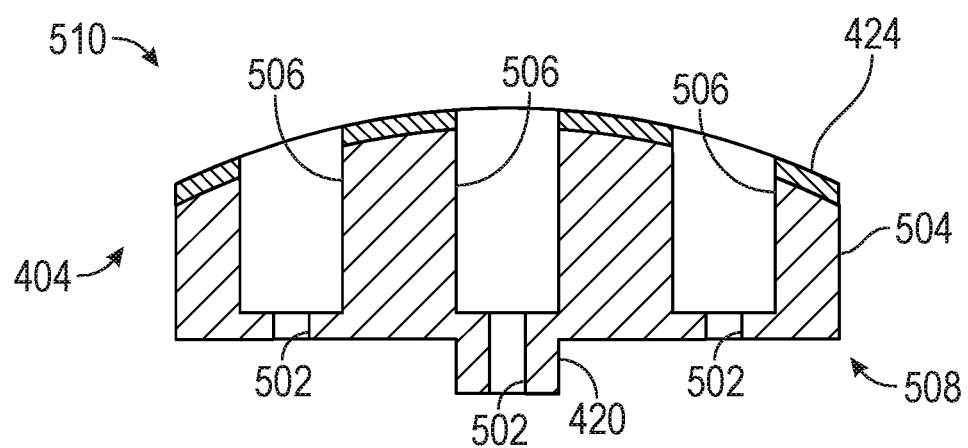
FIG. 5B shows a cross-sectional view of an example glenoid component having a convex articular surface.
Figure 5C:
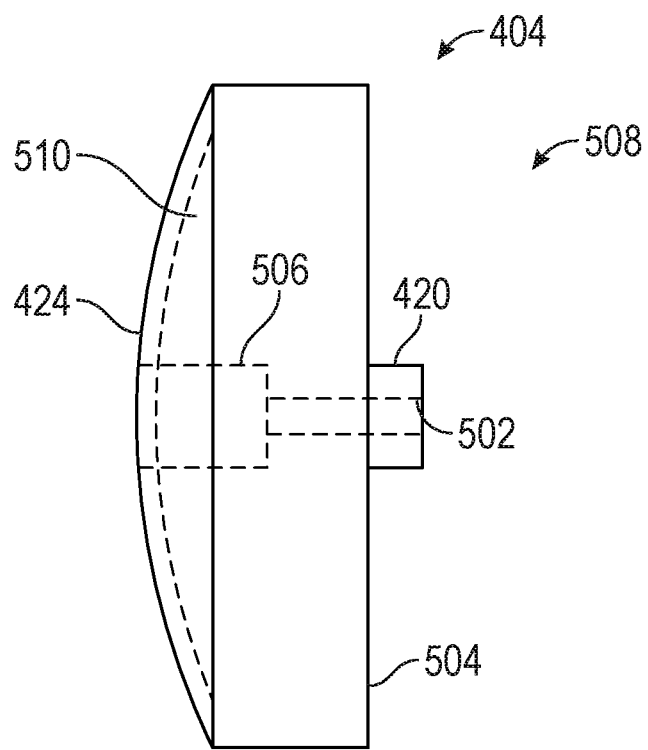
FIG. 5C shows a side view of an example glenoid component having a convex articular surface.

Bone cement 414, bone screws 416, or other fasteners can be used to attach humeral component 402 to humerus 408 and glenoid component 404 to glenoid cavity 410. For example, and as shown in FIGS. 5A-5C humeral component 402 and glenoid component 404 can each include one or more through holes 502. The through holes 502 can allow for fasteners, such as bone screws 416, to pass through humeral component 402 and glenoid component 404 and into humerus 408 and glenoid cavity 410, respectively. Furthermore, bone cement 414 can be placed at various location or coat the distal side of humeral component 402 and the proximal side of glenoid component 404. Bone cement 414 can be used with or without bone screws 416 to attach humeral component 402 to humerus 408 and glenoid component 404 to glenoid cavity 410.

Humeral component 402 can include a humeral peg 418 that extends from the distal side of the component and glenoid component 404 can include a glenoid peg 420 that extends from a proximal side of the component. Humeral peg 418 and glenoid peg 420 can be received within a recess located within humerus 408 and glenoid cavity 410, respectively. The proximal side of humeral component 402 can include a humeral articulation layer 422 and the distal side of glenoid component 404 can include a glenoid articulation layer 424.

Articulation component 406 can be "free floating" and disposed between, but not attached to, humeral articulation layer 422 and glenoid articulation layer 424. As discussed herein, humeral component 402 and glenoid component 404 each can include a convex portion. Articulation component 406 can be ovoid or circular in shape and have corresponding concave portions. Articulation component 406 can rest between the convex portions of humeral component 402 and glenoid component 404. As will be discussed below, during implantation articulation component 406 can be inserted via an incision in an axilla region of a patient. After implantation, articulation component 406 can be held in place by a joint capsule of the shoulder. In addition, as described above regarding articulation component 106, articulation component 406 can be made of a pliable material and inflated within a cavity defined by the humeral component 402 and the glenoid component 404.

As described herein, the various components can be modular and part of a kit of components. For example, as discussed herein, humeral articulation layer 422 can be a separate component from humeral component 402 and glenoid articulation layer 424 can be separate component from glenoid component 404. Glenoid peg 420 and humeral peg 418 can also be separate components. As such, a surgeon can select the appropriate components during a surgery. For instance, during surgery a surgeon may decide to use a convex glenoid component 404 with glenoid articulation layer 424 and a concave humeral component (such as humeral component 102 described above) without a humeral articulation layer.

FIGS. 5A-5C show a glenoid component or a humeral component having convex articular surfaces, in accordance with at least one example of the present application. For simplicity, FIGS. 5A-5C will be referenced with respect to glenoid component 404. However, the discussion of FIGS. 5A-5C also applies to humeral component 402 as well.

Glenoid component 404 can include a component body 504 that can include holes 502. Each of holes 502 can also include a recess 506. The recess 506 can allow screws 416 to be recessed into glenoid component 404. Recess 506 can be filled with a plug or other filler (not shown) after glenoid component 404 has been attached to glenoid cavity 410. Glenoid component 404 can also include glenoid peg 420, which can have a hole 502. Glenoid peg 420 can also be fluted. Glenoid component 404 can be formed of one or more materials. For example, glenoid component 404 can be formed partially of a porous metal, such as tantalum, and partially of a non-porous metal such as stainless steel. Glenoid component 404 can also be formed of a ceramic. Glenoid component 404 can be formed of a highly porous, three-dimensional metallic structure as described with respect to humeral component 102.

A proximal side 508 (sometimes referred to as a medial side) can include glenoid peg 420. In addition, proximal side 508 can be shaped to engage a resected portion of glenoid cavity 410. Proximal side 508 can be flat, concave, or convex. In addition, proximal side 508 can have a custom profile. For example, using imaging techniques such as CT or MRI, glenoid component 404 can be custom designed for a specific patient. As such, a physician can request that proximal side 508 have a mixture of flat, concave, and convex portions to assist with mating glenoid component 404 to glenoid cavity 410.

Glenoid component 404 can also include a distal side 510 (sometimes referred to as a lateral side). Distal side 510 can be convex in shape. The profile of distal side 510 can correspond to a profile of articulation component 406. Having corresponding mating surfaces can allow glenoid component 404 to move freely along articulation component 406.

Glenoid articulation layer 424 can be attached to glenoid component 404. Glenoid articulation layer 424 can be formed on glenoid component 404 via chemical vapor deposition. Glenoid articulation layer 424 can be formed of a ceramic material. Glenoid articulation layer 424 can also be formed of a polymer such as, but not limited to, a vitamin E stabilized polyethylene. A portion of glenoid component 404 can also form glenoid articulation layer 424. For example, a portion of glenoid component 404 can be a polished metal that mates with a concave portion of articulation component 406.

Figure 6:
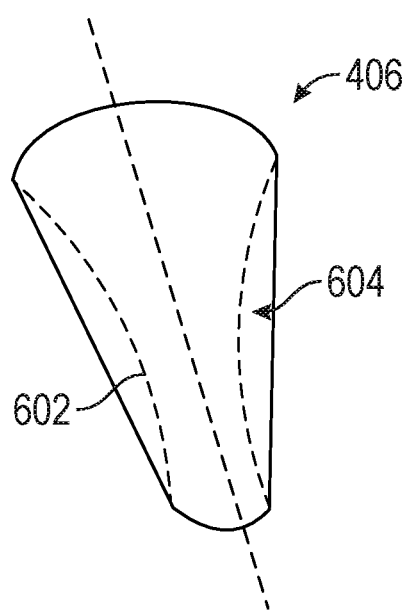
FIG. 6 shows an example articulation component having concave portions.

FIG. 6 shows another articulation component 406 in accordance with at least one example of the present application. Articulation component 406 can be generally spherical in shape. In addition, articulation component 406 can be generally ovoid or circular in shape.

Articulation component 406 can include an outer surface that includes a first portion 602 that can be concave in shape. First portion 602 can be configured to mate with a convex portion of humeral component 402. The outer surface of articulation component 406 can also include a second portion 604 that can be convex in shape. Second portion 604 can be configured to mate with convex portion of distal side 510 of glenoid component 404. In an example, first portion 602 can be convex and second portion 604 can be concave to mate with corresponding concave and convex portions on humeral component 402 and glenoid component 404, respectively. In another example, first portion 602 can be concave and second portion 604 can be convex to mate with corresponding convex and concave portions on humeral component 402 and glenoid component 404, respectively.

Articulation component 406 can be formed of a polymer such as a vitamin E stabilized polyethylene. Articulation component 406 can be formed of a ceramic or metal, such as cobalt chrome. In an example, articulation component 406 can be formed of combinations of a polymer, ceramic, or metal. In an example, articulation component 406 can be formed from a balloon.

Figure 9:
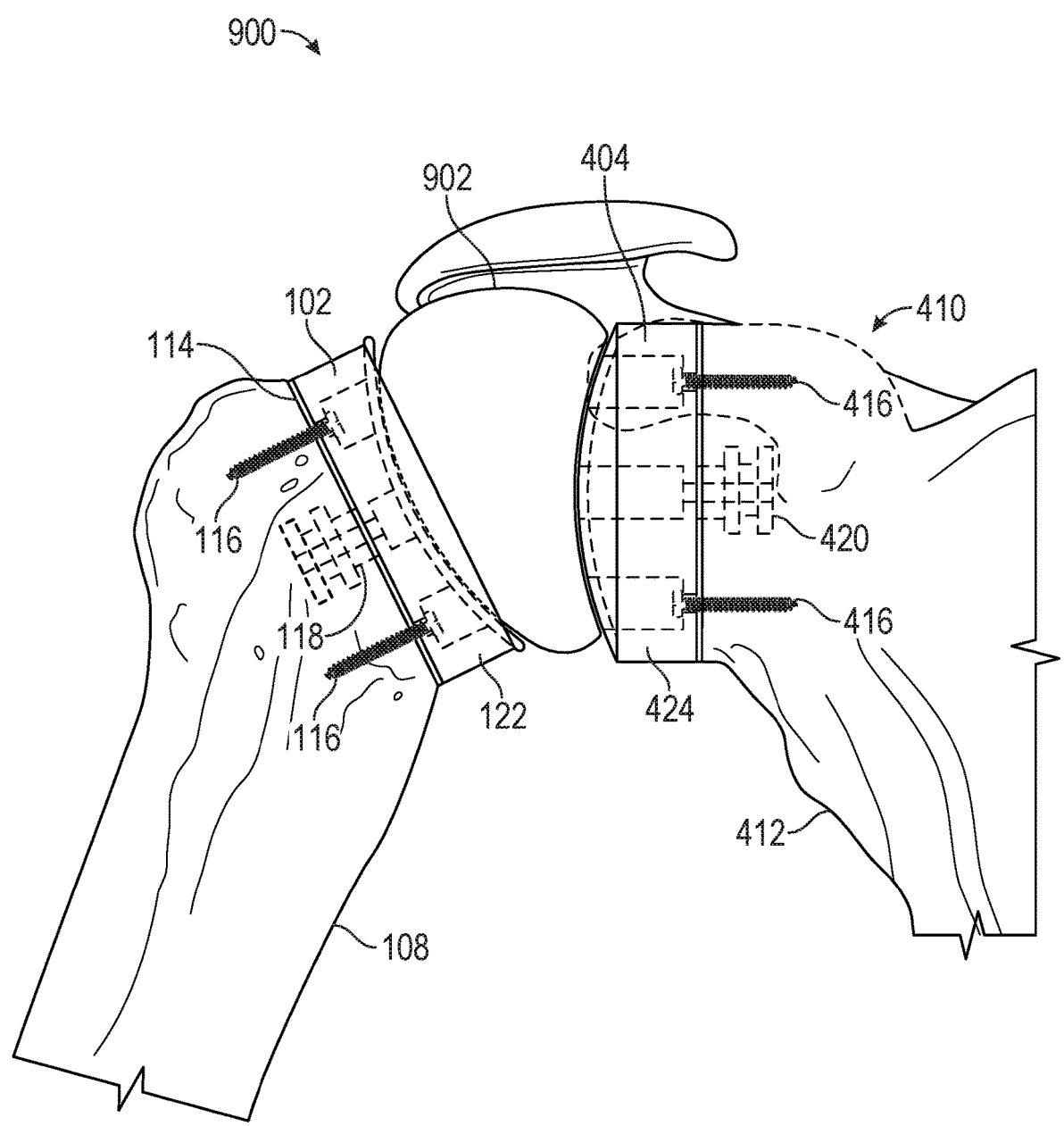
FIG. 9 shows an example of a stemless shoulder implant implanted within a shoulder.

FIG. 9 shows another stemless shoulder implant 900 in accordance with at least one example of the present application. Stemless shoulder implant 900 can include a humeral component 102, a glenoid component 404, and an articulation component 902. Humeral component 102 can be attached to a humerus 108 and glenoid component 404 can be attached to a glenoid cavity 410 of a scapula 412. The interface between humerus 108 and humeral component 102 and the interface between glenoid cavity 410 and glenoid component 404 can be resected bone.

Bone cement 414, bone screws 416 and 116, or other fasteners can be used to attach humeral component 102 to humerus 108 and glenoid component 404 to glenoid cavity 410. For example, and as shown in FIGS. 2A-2C and FIGS. 5A-5C humeral component 102 and glenoid component 404 can each include one or more through holes 202 and 502. The through holes 202 and 502 can allow for fasteners, such as bone screws 116 and 416, to pass through humeral component 102 and glenoid component 404 and into humerus 108 and glenoid cavity 410, respectively. Furthermore, bone cement 114 and 414 can be placed at various locations or coat the distal side of humeral component 102 and the proximal side of glenoid component 404. Bone cement 114 and 414 can be used with or without bone screws 116 and 416 to attach humeral component 102 to humerus 108 and glenoid component 404 to glenoid cavity 410.

Humeral component 102 can include a humeral peg 118 that extends from a distal side of the component and glenoid component 404 can include a glenoid peg 420 that extends from a proximal side of the component. Humeral peg 118 and glenoid peg 420 can be received within a recess located within humerus 108 and glenoid cavity 410, respectively. The proximal side of humeral component 102 can include a humeral articulation layer 122 and the distal side of glenoid component 404 can include a glenoid articulation layer 424.

Articulation component 902 can be "free floating" and disposed between, but not attached to, humeral articulation layer 122 and glenoid articulation layer 424. As discussed herein, humeral component 102 and glenoid component 404 each can include a concave and convex portions. Articulation component 902 can be ovoid or circular in shape and have corresponding convex and concave portions. Articulation component 902 can rest between the concave and convex portions of humeral component 102 and glenoid component 404. As will be discussed below, during implantation articulation component 902 can be inserted via an incision in an axilla region of a patient. After implantation, articulation component 902 can be held in place by a joint capsule of the shoulder. In addition, as described above regarding articulation component 106, articulation component 902 can be made of a pliable material and inflated within a cavity defined by the humeral component 102 and the glenoid component 404.

As described herein, the various components can be modular and part of a kit of components. For example, as discussed herein, humeral articulation layer 122 can be a separate component from humeral component 102 and glenoid articulation layer 424 can be separate component from glenoid component 404. Glenoid peg 420 and humeral peg 118 can also be separate components. As such, a surgeon can select the appropriate components during a surgery. For instance, during surgery a surgeon may decide to use a convex glenoid component 404 with glenoid articulation layer 424 and a concave humeral component 102 without a humeral articulation layer.

Figure 10:
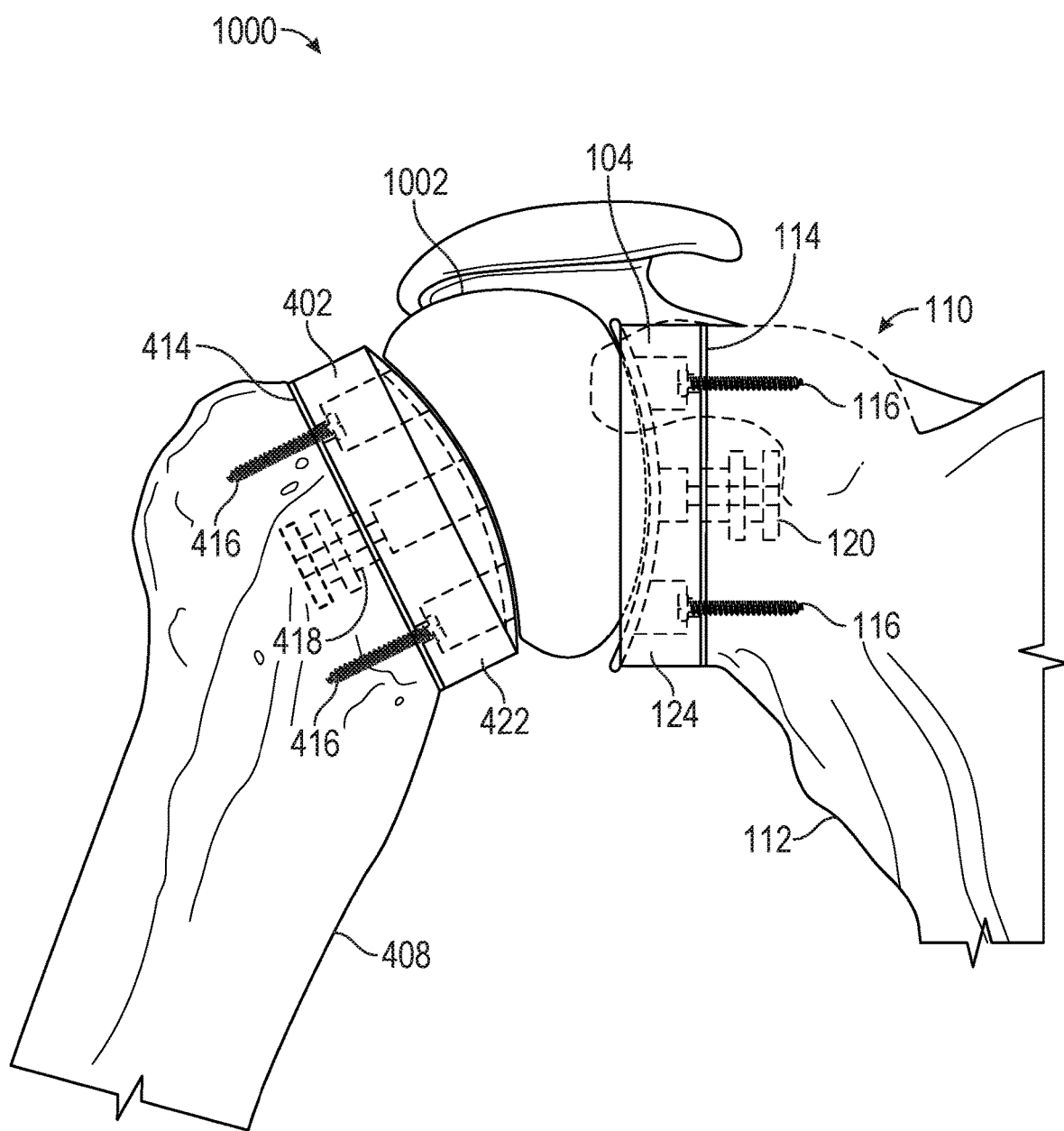
FIG. 10 shows an example of a stemless shoulder implant implanted within a shoulder.

FIG. 10 shows another stemless shoulder implant 1000 in accordance with at least one example of the present application. Stemless shoulder implant 1000 can include a humeral component 402, a glenoid component 104, and an articulation component 1002. Humeral component 402 can be attached to a humerus 408 and glenoid component 104 can be attached to a glenoid cavity 110 of a scapula 112. The interface between humerus 408 and humeral component 402 and the interface between glenoid cavity 110 and glenoid component 104 can be resected bone.

Bone cement 114 and 414, bone screws 116 and 416, or other fasteners can be used to attach humeral component 402 to humerus 408 and glenoid component 104 to glenoid cavity 110. For example, and as shown in FIGS. 2A-2C and 5A-5C humeral component 402 and glenoid component 404 can each include one or more through holes 202 and 502. The through holes 202 and 502 can allow for fasteners, such as bone screws 116 and 416, to pass through humeral component 402 and glenoid component 104 and into humerus 408 and glenoid cavity 110, respectively. Furthermore, bone cement 114 and 414 can be placed at various locations or coat the distal side of humeral component 402 and the proximal side of glenoid component 104. Bone cement 114 and 414 can be used with or without bone screws 116 and 416 to attach humeral component 402 to humerus 408 and glenoid component 104 to glenoid cavity 110.

Humeral component 402 can include a humeral peg 418 that extends from a distal side of the component and glenoid component 104 can include a glenoid peg 120 that extends from a proximal side of the component. Humeral peg 418 and glenoid peg 120 can be received within a recess located within humerus 408 and glenoid cavity 110, respectively. The proximal side of humeral component 402 can include a humeral articulation layer 422 and the distal side of glenoid component 104 can include a glenoid articulation layer 124.

Articulation component 1002 can be "free floating" and disposed between, but not attached to, humeral articulation layer 422 and glenoid articulation layer 124. As discussed herein, humeral component 402 and glenoid component 104 each can include a convex portion. Articulation component 1002 can be ovoid or circular in shape and have corresponding convex and concave portions. Articulation component 1002 can rest between the convex and concave portions of humeral component 402 and glenoid component 104. As will be discussed below, during implantation articulation component 1002 can be inserted via an incision in an axilla region of a patient. After implantation, articulation component 1002 can be held in place by a joint capsule of the shoulder. In addition, as described above regarding articulation component 106, articulation component 1002 can be made of a pliable material and inflated within a cavity defined by the humeral component 402 and the glenoid component 104.

As described herein, the various components can be modular and part of a kit of components. For example, as discussed herein, humeral articulation layer 422 can be a separate component from humeral component 402 and glenoid articulation layer 124 can be separate component from glenoid component 104. Glenoid peg 420 and humeral peg 118 can also be separate components. As such, a surgeon can select the appropriate components during a surgery. For instance, during surgery a surgeon may decide to use a concave glenoid component 404 with glenoid articulation layer 424 and a convex humeral component 102 without a humeral articulation layer.

Figure 7A:
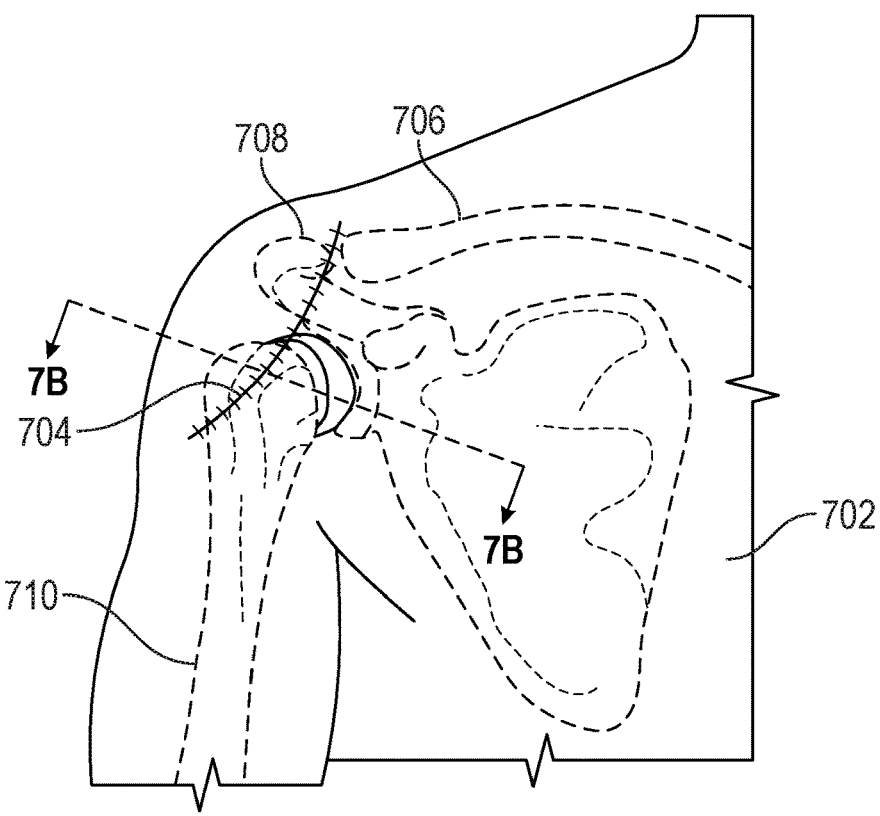
FIG. 7A shows a schematic of a shoulder surgery site using a deltopectoral surgical technique.
Figure 7B:
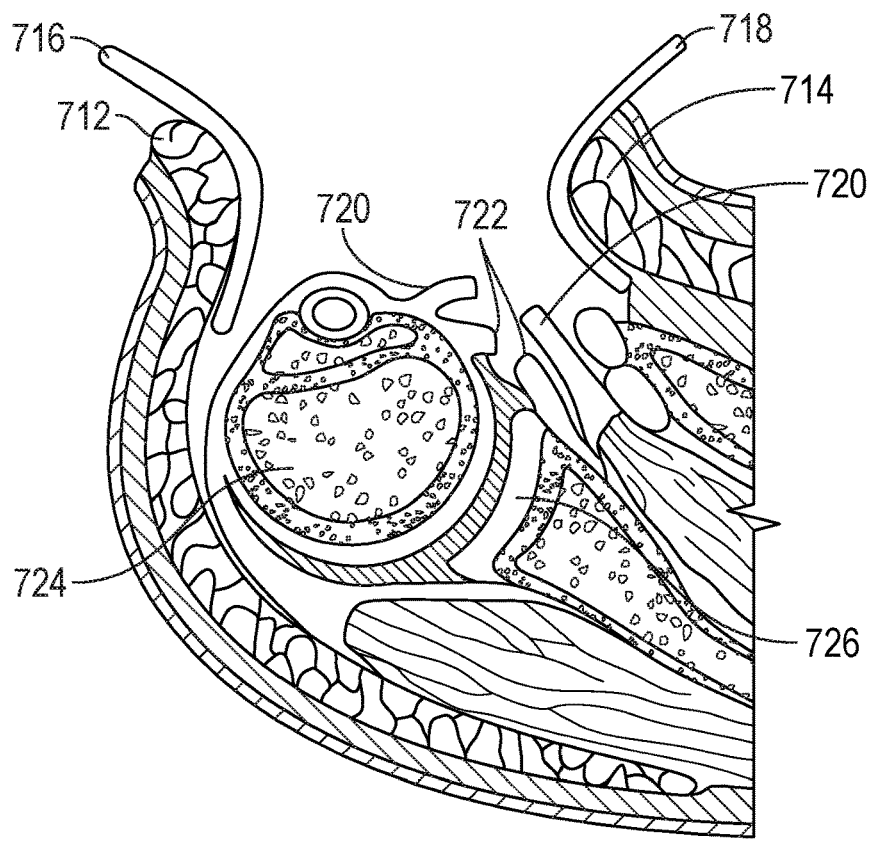
FIG. 7B shows a cross-section of a shoulder joint during a deltopectoral surgical technique.

FIGS. 7A and 7B show a deltopectoral surgical technique in accordance with at least one example of the present application. A patient can lie on his or her back with his or her chest 702 facing up. A surgeon can make an incision along an incision line 704. Incision line 704 can extend from proximal a clavicle 706 and extend across the acromion 708 and past a humerus 710. Once the incision has been made a deltoid muscle 712 and a pectoralis major muscle 714 can be retracted using a first retractor 716 and a second retractor 718, respectively.

Once deltoid muscle 712 and pectoralis major muscle 714 have been retracted, an incision can be made in a subscapularis tendon 720 and an anterior joint capsule 722 to access a humeral head 724 and a glenoid 726. Once humeral head 724 and glenoid 726 have been accessed, humeral head 724 and glenoid 726 can be resected. After resecting humeral head 724, a humeral component, such as humeral component 102 or 402, can be attached to the resected humerus. In addition, after the glenoid is resected at the glenoid cavity, a glenoid component, such as glenoid component 104 or 404, can be attached to the resected glenoid cavity.

The glenoid component and the humeral component can be attached to the glenoid cavity and humerus, respectively, using bone cement, bone fasteners, or a combination thereof. In addition, the glenoid component and the humeral component can each have a peg, such as peg 118, 120, 418, or 420, that can be inserted into a recess cut or drilled into the glenoid cavity or the humerus. The peg can be fluted.

Once the glenoid component and the humeral component have been attached to their respective bones, an articulation component, such as articulation component 106 or 406, can be inserted between the glenoid component and the humeral component. The articulation component can free float between the glenoid component and the humeral component. In other words, the articulation component can be implanted such that it is not attached to either the glenoid component or the humeral component. A rotator cuff, deltoid muscle 712, pectoralis major muscle 714, as well as other tendons and ligaments that make up the joint capsule can hold the articulation component in place between the glenoid component and the humeral component.

Once the articulation component is positioned, subscapularis tendon 720 and anterior joint capsule 722 can be repaired with sutures. Deltoid muscle 712 and pectoralis major muscle 714 can be released by removing first retractor 716 and second retractor 718 and the incision closed with sutures or staples.

Figure 8A:
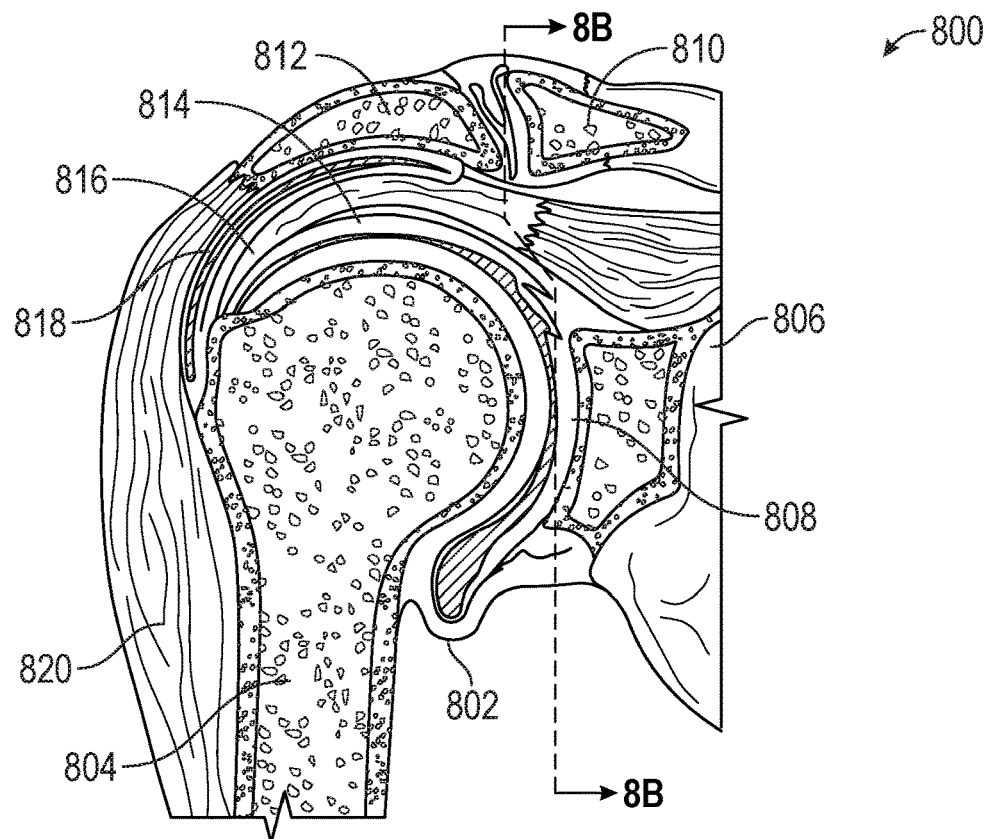
FIG. 8A shows a schematic of a shoulder surgery site using an axilla region surgical technique.
Figure 8B:
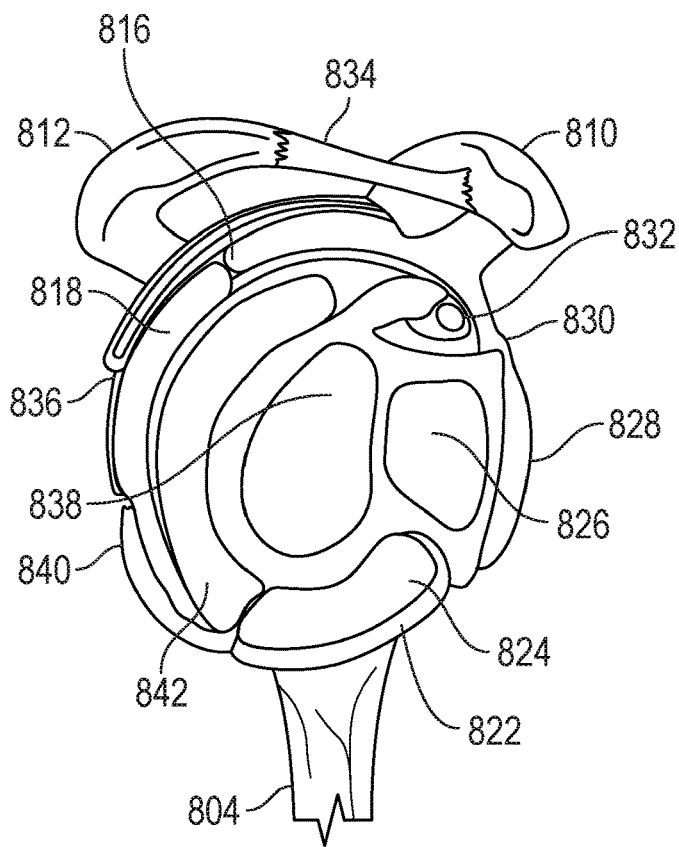
FIG. 8B shows a cross-section of a shoulder joint during an axilla region surgical technique.

FIGS. 8A and 8B show an axillary recess surgical technique in accordance with at least one example of the present application. As shown in FIG. 8A the shoulder joint 800 can include an axillary recess 802, a humerus 804, a scapula 806 having a glenoid cavity 808, a corocoid process 810, an acromion 812, a glenohumeral ligament 814, a supraspinatus tendon 816, a subdeltoid bursa 818, and a deltoid muscle 820. In addition, and as shown in FIG. 8B, shoulder joint 800 can also include an anterior band 822, an inferior glenohumeral ligament 824, middle glenohumeral ligament 826, subscapularis tendon 828, superior glenohumeral ligament 830, a biceps brachit tendon 832, a coracoacromial ligament 834, an infraspinatus tendon 836, glenoid cavity cartilage 838, a teres minor tendon 840, and a posterior band 842.

During surgery, a surgeon can make an incision in an axilla region, such as in axillary recess 802. Once the axilla region has been incised, a portion of humerus 804 and glenoid cavity 808 can be resected through the incision. Additional material, such as for example, glenoid cavity cartilage 838, can be removed from shoulder joint 800 as needed via the incision.

After humerus 804 has been resected, a humeral component, such as humeral component 102 or 402, can be inserted through the incision. The humeral component can include a bone contacting surface and an opposing articular surface.

The humeral component can be attached, via the bone contacting surface of the humeral component to the resected portion of humerus 804. The bone contacting surface of the humeral component can be shaped to mate with the resected portion of humerus 804. The bone contacting surfaces of the humeral component can be at least partially formed from a porous metal. The porous metal can facilitate bone ingrowth after implantation of the humeral component. The bone ingrowth can help solidify attachment of the humeral component to the resected portion of humerus 804.

The humeral component can be attached to the resected portion of humerus 804 by applying bone cement to the bone contacting surface of the humeral component, the resected portion of humerus 804, or both. Alternatively or in addition, the humeral component can be attached to the resected portion of humerus 804 by inserting a bone fastener, such as screws 116 or 416, through the humeral component and into humerus 804.

After glenoid cavity 808 has been resected, a glenoid component, such as glenoid component 104 or 404, can be inserted through the incision. The glenoid component can include a bone contacting surface and an opposing articular surface.

The glenoid component can be attached, via the bone contacting surface of the glenoid component to the resected portion of glenoid cavity 808. The bone contacting surface of the glenoid component can be shaped to mate with the resected portion of glenoid cavity 808.

The glenoid component can be attached to the resected portion of glenoid cavity 808 by applying bone cement to the bone contacting surface of the glenoid component, the resected portion of glenoid cavity 808, or both. Alternatively or in addition, the glenoid component can be attached to the resected portion of glenoid cavity 808 by inserting a bone fastener, such as screws 116 or 416, through the glenoid component and into glenoid cavity 808. The bone contacting surfaces of the glenoid component can be at least partially formed from a porous metal. The porous metal can facilitate bone ingrowth after implantation of the glenoid component. The bone ingrowth can help solidify attachment of the glenoid component to the resected portion of glenoid cavity 808.

Once the humeral component and the glenoid component have been installed, an articulation component, such as articulation component 106 or 406, can be inserted through the incision and between articular surfaces of the humeral component and the glenoid component. The articulation component can be held in between the humeral component and the glenoid component by at least deltoid muscle 820 and a rotator cuff, which can include teres minor tendon 840, infraspinatus tendon 836, and subdeltoid bursa 816. Once the articulation component has been inserted, the incision can be closed.

The surgical technique shown and described with regards to FIGS. 8A and 8B can have advantages over other surgical techniques. For example, the surgical technique shown and described with regards to FIGS. 8A and 8B, sometimes referred to as sub-scap sparing, may not require disturbance of major muscle groups such as, but not limited to, the deltoid muscle, the pectoralis major muscles, and the rotator cuff muscles. In addition, the surgical technique shown and described with regards to FIGS. 8A and 8B may not require incisions in tendons or other ligaments such as, but not limited to, inferior glenohumeral ligament, middle glenohumeral ligament, subscapularis tendon, superior glenohumeral ligament, or biceps brachit tendon. Not disturbing major muscle groups or incising ligaments and tendons can lead to decreased recovery times because the major muscle groups, ligaments, and tendons may suffer less trauma or damage during surgery.

Figure 8C:
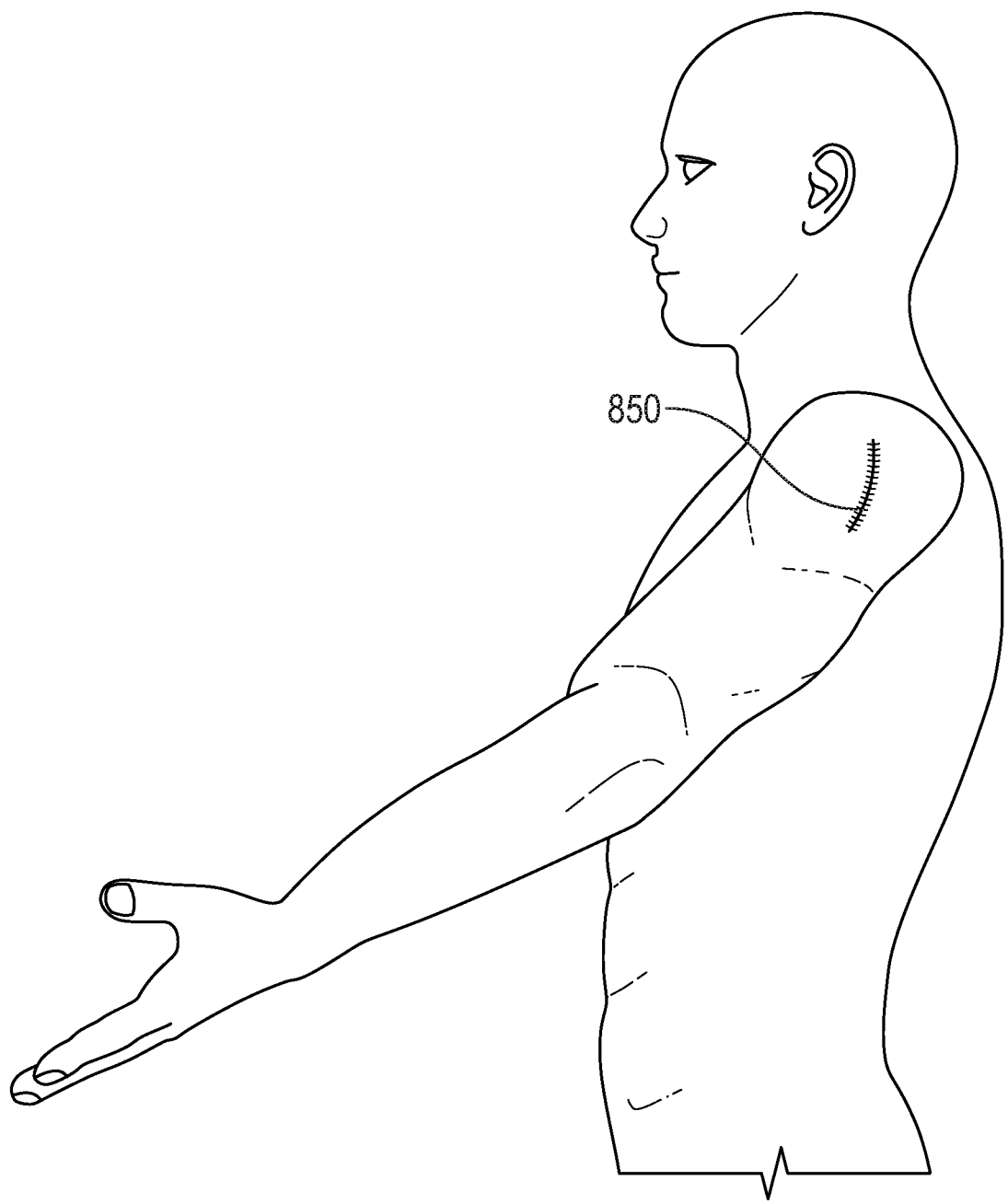
FIG. 8C shows a schematic of a shoulder surgery site using a deltoid splitting technique.

As shown in FIG. 8C, in addition to accessing glenoid cavity 808 and humerus 804 via the axillary recess 802, they can be accessed via an incision 850. Via incision 850 the pectoralis, anterior deltoid, and middle deltoid muscles can be retracted to access glenoid cavity 808 and humerus 804 via deltoid splitting. During the various surgical approaches described herein, the humerus and glenoid cavity can be prepared using reamers and/or saws. For example, a sport's medicine arthroscopic cutter can be used to shape the humerus and the glenoid cavity. In addition, fillers, such as balloons, can be used to fill gaps created during preparations.

It will be readily understood to those skilled in the art that various other changes in the details, material, and arrangements of the parts and method stages which have been described and illustrated in order to explain the nature of the disclosed subject matter may be made without departing from the principles and scope of the disclosed subject matter as expressed in the subjoined claims.

What is claimed is:

1. A shoulder prosthesis comprising:
   a glenoid component including a glenoid body having a proximal side and a distal side, the proximal side shaped to engage with a resected portion of a glenoid cavity;
   a humeral component including a humeral body having a proximal side and a distal side, the distal side shaped to engage with a resected portion of a humerus; and
   an articulation component against which the glenoid component and the humeral component articulate, the articulation component positionable between the distal side of the glenoid component and the proximal side of the humeral component, the articulation component configured to be maintained between the glenoid and humeral components, after implantation, by at least a deltoid muscle and a rotator cuff muscle,
   wherein a cross section of the articulation component has a continuous perimeter forming glenoid and humeral articulation surfaces, a first portion of the continuous perimeter having a first radius of curvature and a second portion of the continuous perimeter located opposite the first portion and having a second radius of curvature, the first radius of curvature being larger than the second radius of curvature, the first portion of the continuous perimeter located proximate an acromion bone when implanted,
   wherein the articulation component is asymmetrical about a centerline that extends from an apex of the second portion of the continuous perimeter to the first portion, and
   wherein the articulation component is asymmetrical about a second axis of the articulation component that extends perpendicular to the first central axis.

2. The shoulder prosthesis of claim 1, wherein the glenoid component further includes a glenoid articular layer on the distal side of the glenoid body, and wherein the humeral component further includes a humeral articular layer on the proximal side of the humeral body.

3. The shoulder prosthesis of claim 2, wherein the glenoid body and the humeral body are at least partially formed from a porous metal.

4. The shoulder prosthesis of claim 3, wherein the porous metal rises tantalum.

5. The shoulder prosthesis of claim 2, wherein at least one of the glenoid articular layer and the humeral articular layer comprises a ceramic material.

6. The shoulder prosthesis of claim 2, wherein at least one of the glenoid articular layer and the humeral articular layer comprises a vitamin E stabilized polyethylene or a cobalt chrome.

7. The shoulder prosthesis of claim 2, wherein the glenoid articular layer and the humeral articular layer each include a concave articular surface.

8. The shoulder prosthesis of claim 7, wherein the glenoid articulation surface of the articulation component includes a first convex portion configured to mate with the concave articular surface of the glenoid articular layer and the humeral articulation surface of the articulation component includes articular a second convex portion configured to mate with the concave articular surface of the humeral articular layer.

9. The shoulder prosthesis of claim 1, wherein the glenoid component and the humeral component are attachable to the resected portion of the glenoid cavity and the resected portion of the humerus, respectively, using bone cement.

10. The shoulder prosthesis of claim 1, wherein the glenoid component and the humeral component are attachable to the resected portion of the glenoid cavity and the resected portion of the humerus, respectively, using one or more fasteners.

11. The shoulder prosthesis of claim 1, wherein at least one of the glenoid component and the humeral component includes a peg configured to be received within a bone recess.

12. The shoulder prosthesis of claim 11, wherein the peg comprises a fluted peg.

13. The shoulder prosthesis of claim 1, wherein the articulation component is at least partially formed from a ceramic, a vitamin E stabilized polyethylene, or a cobalt chrome.

14. The shoulder prosthesis of claim 1, wherein the glenoid body and the humeral body are formed from a first material, and wherein the glenoid articular layer and the humeral articular layer are formed from a second material different than the first material.

15. The shoulder prosthesis of claim 1, wherein the glenoid component includes a fluted peg extending from the proximal side and configured to be received within a bone recess, the glenoid component and the fluted peg defining a screw recess and through hole sized to receive a bone screw.

16. The shoulder prosthesis of claim 15, wherein the humeral component includes a fluted peg extending from the distal side and configured to be received within a bone recess, the humeral component and the fluted peg defining a screw recess and through hole sized to receive a bone screw.

17. The shoulder prosthesis of claim 1, wherein the humeral component includes a fluted peg extending from the distal side and configured to be received within a bone recess, the humeral component and the fluted peg defining a screw recess and through hole sized to receive a bone screw.

* * * * *

UNITED STATES PATENT AND TRADEMARK OFFICE
CERTIFICATE OF CORRECTION

PATENT NO. : 10,828,169 B2
APPLICATION NO. : 15/293373
DATED : November 10, 2020
INVENTOR(S) : Britton et al.

It is certified that error appears in the above-identified patent and that said Letters Patent is hereby corrected as shown below:

On the Title Page

On page 2, in Column 2, under "Other Publications", Lines 12-13, delete "Exarniners" and insert --Examiners-- therefor In the Claims In Column 16, Line 34, in Claim 4, delete "rises" and insert --comprises-- therefor In Column 16, Line 50, in Claim 8, after "includes", delete "articular"

Signed and Sealed this
Nineteenth Day of January, 2021

Andrei Iancu
*Director of the United States Patent and Trademark Office*